United States Patent
Wood et al.

(10) Patent No.: US 9,662,414 B2
(45) Date of Patent: May 30, 2017

(54) DRESSING SYSTEM

(71) Applicants: Edixomed Limited, Edinburgh (GB); First Water Limited, Wiltshire (GB); Queen Mary University of London, London (GB)

(72) Inventors: Christopher Barry Wood, Edinburgh (GB); Hugh Semple Munro, Wiltshire (GB); Nicholas David Boote, Wiltshire (GB); Joanne Ellen Stewart, London (GB); Arthur Tudor Tucker, London (GB)

(73) Assignees: First Water Limited, Marlborough Wiltshire (GB); Queen Mary University of London, London (GB); Edixomed Limited, Edinburgh (GB)

( * ) Notice: Subject to any disclaimer, the term of this patent is extended or adjusted under 35 U.S.C. 154(b) by 0 days.

(21) Appl. No.: 14/892,214

(22) PCT Filed: May 20, 2014

(86) PCT No.: PCT/GB2014/051543
§ 371 (c)(1),
(2) Date: Nov. 19, 2015

(87) PCT Pub. No.: WO2014/188174
PCT Pub. Date: Nov. 27, 2014

(65) Prior Publication Data
US 2016/0082142 A1    Mar. 24, 2016

(30) Foreign Application Priority Data
May 20, 2013 (GB) .................................. 1309091.5

(51) Int. Cl.
| | | |
|---|---|---|
| *A61L 15/00* | (2006.01) | |
| *A61L 15/44* | (2006.01) | |
| *A61L 15/42* | (2006.01) | |
| *A61L 15/60* | (2006.01) | |
| *A61L 15/18* | (2006.01) | |
| *A61L 15/24* | (2006.01) | |
| *A61L 15/26* | (2006.01) | |

(52) U.S. Cl.
CPC ............... *A61L 15/44* (2013.01); *A61L 15/18* (2013.01); *A61L 15/24* (2013.01); *A61L 15/26* (2013.01); *A61L 15/425* (2013.01); *A61L 15/60* (2013.01); *A61L 2300/114* (2013.01); *A61L 2300/204* (2013.01); *A61L 2300/402* (2013.01)

(58) Field of Classification Search
None
See application file for complete search history.

(56) References Cited

U.S. PATENT DOCUMENTS

| | | | |
|---|---|---|---|
| 6,706,279 B1 * | 3/2004 | Hazzi | A61L 26/0052 424/443 |
| 2010/0055161 A1 * | 3/2010 | Ahn | A61K 8/0212 424/449 |
| 2010/0197802 A1 * | 8/2010 | Jezek | A61K 9/70 514/706 |

FOREIGN PATENT DOCUMENTS

| | | |
|---|---|---|
| WO | 0053193 A1 | 9/2000 |
| WO | 0217881 A2 | 3/2002 |
| WO | 2009019498 A2 | 2/2009 |
| WO | 2009019499 A2 | 2/2009 |

OTHER PUBLICATIONS

Friedman et al. (J Clin Aesthet Dermatol. Jun. 2010; 3(6): 45-50).*
Dave et al., Biomedical evaluation of a novel nitrogen oxides releasing wound dressing, J Mater Sci: Mater Med 2012 23:3097-3106.

* cited by examiner

*Primary Examiner* — Robert A Wax
*Assistant Examiner* — Quanglong Truong
(74) *Attorney, Agent, or Firm* — Stradley Ronon Stevens & Young, LLP

(57) ABSTRACT

The present invention provides a system comprising: (i) a layer containing a nitrite; and (ii) a hydrogel that contains hydrogen ions. The invention also provides the use of a system of the invention for the treatment of a condition associated with tissue ischaemia or a wound and the use of a system of the invention in combination with an anaesthetic for the treatment or prevention of pain.

24 Claims, 4 Drawing Sheets

DRESSING SYSTEM

CROSS-REFERENCE TO RELATED APPLICATIONS

This application is a 35 U.S.C. §371 national phase application of PCT Application No. PCT/GB2014/051543, filed May 20, 2014, which claims priority to Great Britain Application No. 1309091.5 filed May 20, 2013, each of which is incorporated herein by reference in its entirety.

FIELD OF THE INVENTION

The present invention relates to skin dressings that are useful in the treatment of conditions associated with tissue ischaemia and skin lesions such as diabetic foot ulcers, burns and surgical wounds.

BACKGROUND TO THE INVENTION

Nitric oxide (NO) is a potent vasodilator, synthesised and released by vascular endothelial cells and plays an important role in regulating local vascular resistance and blood flow. Biologically, nitric oxide (NO) is generated from L-arginine via NO synthase enzymes and performs a variety of functions, including vasodilatation and host defence. NO is also manufactured on epithelial surfaces (such as in the mouth and stomach, and on the skin surface) in humans by sequential reduction of nitrate and nitrite. This relies on the synthesis of nitrite by the bacterial reduction of inorganic nitrate present in saliva, mucosal secretions or sweat. Nitrite is further reduced to NO in an acidic environment.

The combination of acid and nitrite is effective in killing a wide variety of pathogens by the generation of NO and oxides of nitrogen. It is likely that NO generated in this way has a significant role in host defence against microbial pathogens, many of which are known to be susceptible to this agent.

A system has previously been devised that mimics this endogenous mechanism of NO generation, using inorganic nitrite and an organic acid to produce NO on the skin surface. This method relies on keeping the components separate until applied directly to the skin. When used in this way, the system is effective in treating infectious skin disease and increasing skin blood flow. Individually, these components elicit no significant effects.

WO 2000/053193 relates to the use of acidified nitrite as an agent to produce local production of nitric oxide at the skin surface for the treatment of peripheral ischaemia and associated conditions such as Raynaud's phenomenon and wounds such as post-operative wounds and burns. In some embodiments, a barrier consisting of a membrane allows diffusion of the nitrite ions while preventing direct contact of the skin and acidifying agent.

SUMMARY OF THE INVENTION

The present inventors have developed an improved dressing system that is useful in the treatment of conditions associated with tissue ischaemia and skin lesions such as diabetic foot ulcers, burns and surgical wounds. The dressing makes use of a hydrogel to provide the acidifying effect on a nitrite for the production of NO. The use of a hydrogel is advantageous as it can be placed directly in contact with the skin and can absorb exudates from wounds.

Accordingly, in a first embodiment the present invention provides a system comprising:
(i) a layer containing a nitrite; and
(ii) a hydrogel that contains hydrogen ions.

DETAILED DESCRIPTION OF THE INVENTION

The system of the invention is a dressing system. A "dressing", as will be well known to a person of skill in the art, is something that is applied to the skin of a human or animal to cover, protect and/or treat a lesion on the skin of the human or animal. A dressing is suitable for use in relation to any breakage or interruption in the skin barrier, which can be caused, for example, by ulcers, surgery, burns, cuts, lacerations, trauma and/or abrasions.

The system of the invention is a two component system, comprising a first component which comprises a layer containing a nitrite and a second component comprising a hydrogel that contains hydrogen ($H^+$) ions and therefore has an acidic pH. The two components can in fact be considered as two separate dressings. When the two components are placed in contact with each other, a chemical reaction takes place to produce nitric oxide (NO). The two components will now be described in detail.

The first component of the system of the invention comprises or is a layer containing a nitrite. The layer is permeable (fully permeable or at least semi-permeable) to the diffusion of nitric oxide, which forms when the first and second components of the dressing are placed in contact with each other. The first component of the system of the invention is typically placed in direct contact with the skin (i.e. on a wound or ulcer) during use, and should not adhere to the skin and/or cause damage to the wound bed or friable wound tissue. The layer can therefore be described as a wound contact layer. The layer can therefore be made of any material that is suitable for this purpose and which can be impregnated with, imbibed with or otherwise contain a nitrite. The layer is typically, but not limited to, a mesh, non-woven bat, film, foam, alginate, amorphous hydrogel, crosslinked hydrogel or a membrane.

In one embodiment, the layer is a mesh. A mesh consists of connected strands of solid, typically flexible material, that form a lattice with holes or gaps through which certain substances can pass. The mesh can be woven or non-woven, but is typically non-woven.

The mesh is typically made of a polymeric material. Any polymeric material is suitable, for example viscose, polyamide, polyester, polypropylene or blends of these, but a preferred polymeric material is polypropylene.

In some embodiments, the system of the invention comprises a plurality of (i.e. more than one) layers containing a nitrite. For example, the system of the invention can comprise 2, 3, 4, 5, 6, 7, 8, 9 or 10 or more layers containing a nitrite. For example, the system of the invention can comprise a plurality of meshes imbibed with a nitrite, for example as a nitrite solution. Typically, when a plurality of layers is used, each of the layers is formed of the same material, for example a mesh.

In one embodiment, the layer is not a membrane and/or a gel, for example a hydrogel.

The layer contains a nitrite salt in solid or solution form. Typically, the nitrite is in the form of a nitrite solution. The layer is typically imbibed or impregnated with the nitrite, for example by soaking the layer in a solution of the nitrite. The nitrite is typically a pharmacologically acceptable source of nitrite ions or a nitrite precursor thereof.

The layer (such as a mesh) functions to retain the nitrite solution essentially within a region defined by the area of the layer (such as a mesh). This provides for ease of application of the dressing to the skin and/or wound.

The pharmacologically acceptable source of nitrite ions may be an alkaline metal nitrite or an alkaline earth metal nitrite. For example, $LiNO_2$, $NaNO_2$, $KNO_2$, $RbNO_2$, $CsNO_2$, $FrNO_2$, $Be(NO_2)_2$, $Mg(NO_2)_2$, $Ca(NO_2)_2$, $Sr(NO_2)_2$, $Ba(NO_2)_2$, or $Ra(NO_2)_2$. In a preferred embodiment the nitrite is sodium nitrite ($NaNO_2$).

Alternatively, a nitrite precursor may be used as the source of the nitrite ions in the composition, such as for example a dilute solution of nitrous acid. Other sources of nitrite ions are nitrate ions derived from alkali metal or alkaline earth metal salts capable of enzymic conversion to nitrite. For example, $LiNO_3$, $NaNO_3$, $KNO_3$, $RbNO_3$, $CsNO_3$, $FrNO_3$, $Be(NO_3)_2$, $Mg(NO_3)_2$, $Ca(NO_3)_2$, $Sr(NO_3)_2$, $Ba(NO_3)_2$, or $Ra(NO_3)_2$.

The concentration of the nitrate/nitrite ion source may be up to 20% w/w, suitably 0.25 to 15%, suitably 2 to 12%, suitably 4 to 10%, for example 5 to 8%. A particularly preferred concentration is 6% to 7% w/w.

Suitably, the final nitrite ion concentration present in the composition is up to 20% w/w, generally in the range of from 0.25% to 15% w/w, for example 0.5% to 14% w/w, 1% to 13% w/w, suitably 2% to 12% w/w, suitably 3% to 11% w/w, suitably 4 to 10% w/w or 5 to 8% w/w. A particularly preferred nitrite ion concentration is 6% to 7% w/w.

If a solution of nitrite ions is being used, the molarity of the solution is typically from 0.01M to 2M, for example from 0.1M to 2M, for example from 0.2M to 1.8M, from 0.3M to 1.7M, from 0.4M to 1.6M, from 0.5M to 1.5M, for example around 0.7M, 0.8M, 0.9M, 1M, 1.1M, 1.2M or 1.3M.

In one specific embodiment, the first component of the dressing system is a polypropylene mesh or a plurality of polypropylene meshes impregnated with sodium nitrite, typically as a sodium nitrite solution.

In certain embodiments of the invention, which can optionally comprise a reductant, the amount (weight or volume) of nitrite solution can be used to control the amount of nitric oxide produced over time. Preferred amounts of sodium nitrite solution are from 5 mg to 100 mg per $cm^2$ of the area of nitrate containing layer (for example mesh) in contact with the hydrogen ion donating hydrogel, for example from 10 mg to 85 mg per $cm^2$, from 20 mg to 75 mg per $cm^2$, from 30 mg to 60 mg per $cm^2$ or from 10 mg to 85 mg per $cm^2$.

The second component of the dressing system of the invention is a hydrogel that contains hydrogen ($H^+$) ions and is therefore acidic. Hydrogen ($H^+$) ions can alternatively be referred to as protons. By virtue of the presence of hydrogen ions, the hydrogel reduces the pH at the site of application. The preferred pH range is from pH2 to pH7, preferably from pH3 to pH6, more preferably from pH3.5 or pH4 to pH5, more preferably around pH4, for example from pH4.2 to pH4.6. When the hydrogel is placed in contact with the layer containing a nitrite, the acidic environment created by the hydrogel allows the chemical reaction that produces nitric oxide from nitrite to take place. Thus, when the hydrogel is placed in contact with the layer containing a nitrite, nitric oxide is produced which diffuses through the layer containing a nitrite and onto or into the skin or wound bed of the patient.

It can therefore be seen that the two components of the system of the invention are typically kept apart until use, to prevent nitric oxide from being generated prematurely.

Without wishing to be bound by theory, when the hydrogel is placed on top of the first component of the system (the layer or layers containing a nitrite), hydrogen ions (which are normally bound within the gel) are released and diffuse down a concentration gradient through the hydrogel and into the layer containing a nitrite, where they react with the nitrite to produce nitric oxide. A second process occurs where the hydrogel absorbs the nitrite solution or layer containing the nitrite and the reaction takes place at the surface of or within the hydrogel; the nitric oxide is released from the hydrogel through the layer containing the nitrite into the tissue.

Hydrogels suitable for use in wound dressings are typically three-dimensional networks of cross-linked hydrophilic polymers that are insoluble in water and interact with aqueous solutions by swelling. They are highly conformable and permeable and can absorb varying amounts of fluid depending on their composition. In some embodiments, the hydrogel of the invention belongs to the category of materials described as super-absorbent.

The hydrogel for use in the present invention contains hydrogen ($H^+$) ions. Suitable hydrogels for use in the present invention therefore include one or more components that are proton ($H^+$ ion) donors, for example carboxylic acid groups. Typically the monomer or one of the monomers (when the hydrogel is a co-polymer) present in the hydrogel acts as a proton donor. In the present invention the counter-ion to the hydrogen ion is typically bound into the three-dimensional polymer network of the hydrogel and is not released into the wound.

In one embodiment, the hydrogel is a co-polymer, i.e. a polymer made up of two or more different monomer components. As described above, the hydrogel includes components that are proton donors, for example carboxylic acid groups. Suitable hydrogels therefore include polymers and co-polymers of carboxylic acids such as acrylic acid (ethylenecarboxylic acid) and methacrylic acid (2-methyl-2-propenoic acid).

Another suitable component of the hydrogel when it is a co-polymer is 2-acrylamido-2-methylpropane sulfonic acid (AMPS™, Lubrizol Corporation).

The $pK_a$ of acrylic acid is 4.3 to 4.4, which is similar to the pH of the hydrogel. Accordingly, in one embodiment, the $pK_a$ of the monomer or one of the monomers in the hydrogel is within 1 unit of the pH, typically the surface pH, of the hydrogel. Accordingly, in one embodiment, the $pK_a$ of the monomer or one of the monomers in the hydrogel is the same or essentially the same as the pH of the hydrogel, typically the surface pH of the hydrogel.

In one embodiment, the hydrogel is partially hydrated, i.e. it contains some water. This means that the hydrogel provides a moist environment that assists the healing of a wound or ulcer. In certain embodiments, the hydrogel contains from 5% to 50%, for example from 10% to 40%, for example from 15% to 35%, for example from 20% to 30% or around 30% water by weight of the hydrogel.

The hydrogel typically contains the polymer as its major component. For example, the hydrogel can contain from 10% to 60%, for example from 20% to 50%, for example from 30% to 45%, for example around 40% of the polymer by weight of the hydrogel.

The hydrogel may contain other components, as desired. For example, the hydrogel may contain other components in addition to the monomer or monomers from which its polymeric structure is composed. Additional components such as glycerol may be present. Such additional components may make up a substantial amount of the hydrogel. For example, the hydrogel can contain from 5% to 50%, for example from 10% to 40%, for example from 15% to 35%, for example from 20% to 30% or around 30% of glycerol by weight of the hydrogel.

The hydrogel may contain a pH buffer to maintain the pH in the range 2-7. However, the addition of a pH buffer is typically not required.

In one specific embodiment, the hydrogel is a cross-linked co-polymer of a sulfonate and acrylic acid or methacrylic acid and in particular the hydrogel co-polymer available from First Water Ltd as the FW206 class of hydrogels.

This hydrogel comprises circa 40% of a cross-linked anionic copolymer, circa 30% water and circa 30% glycerol.

The thickness of the hydrogel is typically up to 4 mm, typically 0.5-2 mm, more typically 1-2 mm, even more typically 1-1.6 mm.

In one embodiment, the hydrogel contains a solid layer within it to provide mechanical strength, for example for processing purposes. The solid layer can be made of any suitable material and in one embodiment is a mesh, suitably made of a polymer, suitably a polypropylene mesh. The solid layer is suitably provided in the middle of the hydrogel, for example in the form of a "sandwich" wherein the solid layer is sandwiched in between two layers of hydrogel.

In one embodiment, the hydrogel has a barrier layer, for example a film such as a polyurethane film or an adhesive coated polyurethane film, on one of its external surfaces, typically on the surface that will be exposed to the air when in use. This layer typically provides a bacterial barrier.

In use, the second component of the dressing system is placed on top of the first component of the dressing system. The second component has a number of functions. Firstly, by virtue of the presence of hydrogen ions, the second component creates an acid environment for the conversion of nitrite to nitric oxide. Also, the second component of the dressing system is typically larger than the first component, and is of a suitable size and shape that when it overlays the first component it entirely covers the first component, such that there is an area on one or more of its edges, and typically all the way round the first component, that is in contact with the skin of the patient. The second component is adhesive and so, in this configuration, the second component retains the first component in place on the skin of a patient, typically over an ulcer or wound, in a manner analagous to that of a plaster (or BandAid™).

Since the system of the invention is a dressing useful for the treatment of ulcers and wounds, it is adapted for transdermal administration. The components of the system of the invention may be prepared by any method known in the art of pharmacy, and are typically prepared under sterile conditions.

The system of the invention is a two component system, comprising a first component which comprises a layer or a plurality of layers containing a nitrite and a second component comprising a hydrogel that contains hydrogen ($H^+$) ions. In one embodiment, the system of the invention does not contain any other components. In this embodiment, the system consists of or consists essentially of a first component which comprises a layer or a plurality of layers containing a nitrite and a second component comprising a hydrogel that contains hydrogen ($H^+$) ions. In one embodiment, the first component consists of or consists essentially of a (typically permeable) layer or plurality of layers containing a nitrite. In another embodiment, the second component consists of or consists essentially of a hydrogel that contains hydrogen ($H^+$) ions.

The system of the invention preferably does not contain certain other substances. In particular, the system itself or one or both of its components preferably does not contain a thiol and/or a reductant, typically a non-thiol reductant, or only contains these substances in trace amounts, i.e. less than 0.05%, typically less than 0.01%, more typically less than 0.005% by weight of the system, or one or both components thereof. Thiols include glutatione (typically L-glutathione), 1-thioglycerol, 1-thioglucose, cysteine, and methyl- or ethyl-ester of cysteine, N-acetylcysteine, mercaptoethylamine and 3-mercaptopropanoic acid. Non-thiol reductants include iodide anion, butylated hydroquinone, tocopherol, butylated hydroxyanisole, butylated hydroxytoluene and beta-carotene, erythrobate or α-tocopherol, ascorbic acid (vitamin C). In some embodiments, the system itself or one or both of its components does not contain a source of $Cu^{2+}$ $Zn^{2+}$ and/or $Fe^{2+}$ ions.

In one embodiment, the first component does not contain a thiol and/or a reductant, typically a non-thiol reductant. In another embodiment, the second component does not contain a thiol and/or a reductant, typically a non-thiol reductant. In another embodiment, both the first component and the second component do not contain a thiol and/or a reductant, typically a non-thiol reductant.

In one embodiment, the first component does not contain a source of $Cu^{2+}$ $Zn^{2+}$ and/or $Fe^{2+}$ ions. In another embodiment, the second component does not contain a source of $Cu^{2+}$ $Zn^{2+}$ and/or $Fe^{2+}$ ions. In another embodiment, both the first component and the second component do not contain a source of $Cu^{2+}$ $Zn^{2+}$ and/or $Fe^{2+}$ ions.

The dressing system of the invention has two active components: the hydrogel which contains $H^+$ ions; and the nitrite. No other active components are necessary for the functioning of the dressing system of the present invention.

The dressing system of the present invention has a number of advantages over those known in the art. Firstly, the use of the hydrogel to provide the acidifying component for production of the nitric oxide has the advantage that it can be placed in direct contact with the skin, in contrast with the prior art systems where the acidifying agent is typically not suitable for direct contact with the skin and therefore it is often suggested to provide a membrane to prevent contact of the acidifying agent with the skin. In contrast, the system of the present invention can be kept in contact with the skin for prolonged periods of time, which represents a significant advantage. This feature of the hydrogel and also its physical properties means that it can be used to secure, trap or fix the underlying nitrite-imbibed layer in place on the skin of a patient, in a manner analagous to that of a sticking plaster (or BandAid™), thus allowing the correct positioning of the nitrite-containing layer. This also has the advantage that the amount of nitric oxide produced can be controlled by changing the volume of nitrite solution imbibed by the layer or layers containing the nitrite, which is/are then held in place by the hydrogel, as demonstrated in Examples 6 and 7. This is an advantage of the use of a nitrite solution together with a hydrogel. Another advantage of the use of the hydrogel is that it is useful for absorbing exudate (i.e. blood, plasma and other fluids) from wounds and thus can be used to keep the wound clean. The hydrogel also keeps the wound moist (whilst not allowing it to become "wet"), which promotes healing. A further advantage of the dressing system of the invention is that bubbles are not produced, thus creating a more aesthetically pleasing dressing. The dressing system of the present invention thus provides a system that is easy to apply, well tolerated by patients and provides a controlled environment for the chemical reaction in which NO is produced.

The present inventors have also surprisingly found that the amount and profile of nitric oxide release is not necessarily linear with the amount or molarity of the nitrite solution, as shown in Examples 6 and 7. The rate and amount of nitric oxide produced by the dressing system of the invention can therefore be controlled by varying the amount of nitrite in the layer or layers that form the first component of the system of the invention, for example by using a plurality of layers imbibed with nitrite solution, changing the molarity of the nitrite solution or changing the thickness of the layer or layers imbibed with a nitrite solution.

In a second aspect, the present invention provides the system of the first aspect of the invention for use in medicine.

In a third aspect, the present invention provides the system of the first aspect of the invention for use in the treatment of a condition associated with tissue ischaemia or a wound. This aspect of the invention also extends to the use of a layer containing a nitrite and a hydrogel that contains hydrogen ions in the manufacture of a medicament for the treatment of a condition associated with tissue ischaemia or a wound.

This aspect of the invention also extends to:

A layer containing a nitrite for use in the treatment of a condition associated with tissue ischaemia or a wound, wherein said layer is administered simultaneously, separately or sequentially with a hydrogel that contains hydrogen ions.

A hydrogel that contains hydrogen ions for use in the treatment of a condition associated with tissue ischaemia or a wound, wherein said hydrogel is administered simultaneously, separately or sequentially with a layer containing a nitrite.

Use of a layer containing a nitrite in the manufacture of a medicament for the treatment of a condition associated with tissue ischaemia or a wound, wherein said layer is administered simultaneously, separately or sequentially with a hydrogel that contains hydrogen ions.

Use of a hydrogel that contains hydrogen ions in the manufacture of a medicament for the treatment of a condition associated with tissue ischaemia or a wound, wherein said hydrogel is administered simultaneously, separately or sequentially with a layer containing a nitrite.

A system comprising a layer containing a nitrite and a hydrogel that contains hydrogen ions as a combined preparation for simultaneous, separate or sequential use in treating a condition associated with tissue ischaemia or a wound.

This aspect of the invention also extends to a method of treatment of a condition associated with tissue ischaemia or a wound comprising administering a system of the first aspect of the invention to a subject in need thereof. The subject is a patient having a condition associated with tissue ischaemia or a wound, as described herein. The method typically comprises administering to the patient the first component described herein and then subsequently administering the second component described herein, on top of the first component. Tissue ischaemia is a restriction to the blood supply in tissues. In some embodiments, the tissue ischaemia is peripheral ischaemia, i.e. where peripheral circulation is restricted, for example skin ischaemia.

In some circumstances, damage to the skin leads to tissue ischaemia as the blood supply is reduced or prevented by the body's own repair or defence mechanisms.

Conditions associated with tissue ischaemia include Raynaud's syndrome, severe primary vasospasm and tissue ischaemia caused by septic shock or irradiation, as well as post-surgical tissue ischaemia.

The present invention is also useful in the treatment of wounds. Wounds include ulcers, skin donor sites, surgical wounds (post-operative), burns (for example scalds, superficial, partial thickness and full thickness burns), lacerations and abrasions, and can be chronic or acute. Some burns (for example full thickness and some partial thickness burns) are also associated with tissue ischaemia. Ulcers can be of various origin, for example of venous or arterial origin, and include leg ulcers, pressure ulcers, venous ulcers and diabetic ulcers such as diabetic foot ulcers.

Dosages of nitric oxide, which is the active substance produced by the system of the present invention, can vary between wide limits, depending upon the disease or disorder to be treated, the severity of the condition, and the age and health of the individual to be treated, etc. and a physician will ultimately determine appropriate dosages to be used. The system is configured so as to deliver nitric oxide in a therapeutically active amount, which is an amount that ameliorates or eliminates the symptoms of the condition (such as an ulcer or wound) that is being treated. As described herein, the system of the present invention can be used to control the amount and duration of nitric oxide release.

This dosage may be repeated as often as appropriate. If side effects develop the amount and/or frequency of the dosage can be reduced or otherwise altered or modified, in accordance with normal clinical practice.

The system of the invention may be formulated for use in human or for veterinary medicine. The present application should be interpreted as applying equally to humans as well as to animals, unless the context clearly implies otherwise.

In a fourth aspect, the present invention provides a kit comprising a layer containing a nitrite and a hydrogel that contains hydrogen ions as a combined preparation for simultaneous, separate or sequential use in treating a condition associated with tissue ischaemia or a wound. The kit is suitably provided with instructions for use in the treatment of a condition associated with tissue ischaemia or a wound.

The present inventors have also found that when applied as a pre-treatment, a dressing system of the invention functions to increase the effectiveness of a topically applied aqueous-soluble anaesthetic. The system of the invention can therefore also be used in combination with an aqueous-soluble drug such as an anaesthetic when the dressing system is administered simultaneously with the drug (such as an anaesthetic) or after the drug (such as an anaesthetic).

Accordingly, in a fifth aspect, the present invention provides the system of the first aspect of the invention in combination with an aqueous-soluble drug for use in medicine.

By "aqueous-soluble drug" is meant one that for each part of the drug will require 1000 parts or less of an aqueous solvent to solubilise it. In other words, the drug is at least slightly soluble in accordance with the definition given in The United States Pharmacopeia, USP 30-NF 25, 2007 and British Pharmacopoeia, 2009. For example, lidocaine hydrochloride is soluble on this scale requiring 20 parts water to 1 part lidocaine.

Examples of aqueous-soluble drugs for use in accordance with this aspect of the invention include the anti-hypertensive, Atenolol, the water soluble antibiotics, Ampicillin, Streptomycin, Penicillin and the naturally water-soluble vitamins, specifically B and C.

In a sixth aspect, the present invention provides the system of the first aspect of the invention in combination with an anaesthetic for use in the treatment or prevention of pain.

The anaesthetic can be any appropriate anaesthetic for local anaesthesia and is typically selected from the group consisting of lignocaine (lidocaine), amethocaine (tetracaine), xylocaine, bupivacaine, prilocaine, ropivacaine, benzocaine, mepivocaine, cocaine or a mixture thereof. The anaesthetic is typically provided in aqueous or powdered form. For example, anaesthetics such as lidocaine hydrochloride can be provided in the form of a spray of the drug in aqueous form.

The treatment or prevention of pain is typically local anaesthesia but can be the treatment or prevention of any kind of pain. Pain includes chronic and acute pain, post-operative pain and neuropathic pain. Treatment includes both amelioration and prevention (prophylaxis) of pain.

The general concentration range is around 1 to 4%, up to 10% w/w, although greater or lesser amounts can be empirically determined by a physician. Suitably preferred concentrations are tetracaine (0.01 to 10% w/w, suitably 1 to 8% w/w, preferably 2% w/w), lidocaine (0.01 to 10% w/w, suitably 1 to 8% w/w, preferably 5% or 10% w/w) and cocaine (1 to 4% w/w). Generally accepted safe dosages of such compounds for topical anaesthesia in a healthy 70 kg-adult are 750 mg for lidocaine, 200 mg for cocaine, and 50 mg for tetracaine. Other suitable anaesthetics are within the competence of the medical practitioner and can also be used in the system of the present invention at the relevant concentrations.

This aspect of the invention also extends to:

A system of the first aspect of the invention for use in the treatment or prevention of pain, wherein said system is administered simultaneously, separately or sequentially with an anaesthetic.

Use of a system of the first aspect of the invention in the manufacture of a medicament for the treatment or prevention of pain, wherein said system is administered simultaneously, separately or sequentially with an anaesthetic.

This aspect of the invention also extends to a method of treatment or prevention of pain comprising administering a system of the first aspect of the invention and an anaesthetic to a subject in need thereof.

The subject is a patient suffering from pain, or one who is likely to suffer from pain in the future (and therefore is in need of anaesthetic). The method typically comprises either administering to the patient the system of the first aspect of the invention (as a pre-treatment) and then subsequently administering an aqueous-soluble drug such as an anaesthetic, or administering to the patient an aqueous-soluble drug such as an anaesthetic and then subsequently administering the patient the system of the first aspect of the invention. Alternatively, the system of the first aspect of the invention and the aqueous-soluble drug such as an anaesthetic are administered simultaneously.

Preferred features for the second and subsequent aspects of the invention are as for the first aspect mutatis mutandis.

The present invention will now be described by way of illustration only with reference to the following Examples and Figures, in which.

EXAMPLE 1

Figure 1:
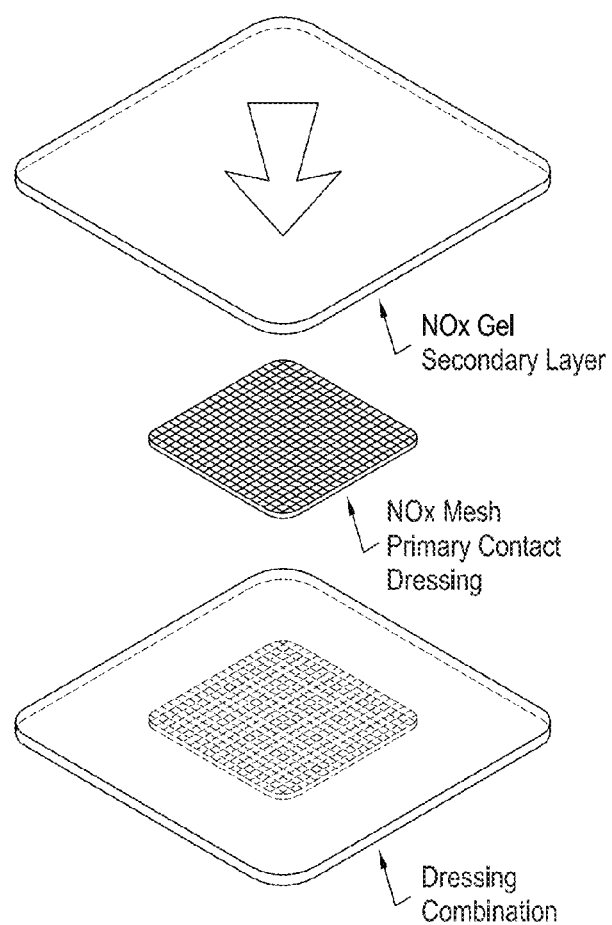
FIG. 1 is a schematic diagram of the system of the present invention

Production of Dressing System of the Invention

Primary Layer: Wound Contact Mesh (containing 1M Sodium Nitrite)

The Mesh is a polypropylene mesh (RKW-Group), imbibed with 1M Sodium Nitrite solution, from Sodium Nitrite Extra Pure ph Eur, USP Merck and deionised water.

Description of Manufacturing Process

Sodium nitrite is weighed into a suitably sized vessel and then transferred carefully into a known volume of deionised water, which is then stirred until dissolution is complete to make a solution of appropriate concentration. In this embodiment the sodium nitrite solution is dispensed onto the mesh and then is placed into each petri dish for a minimum time to imbibe the mesh with the sodium nitrite solution. The finished products are sterilised by irradiation.

Secondary Layer: Hydrogel Top Layer

The hydrogel chosen for this study has high capability for absorption and facilitates a moist wound-healing environment. The hydrogel comprises a cross-linked anionic copolymer, circa 30% water and circa 30% glycerol. It has an integral polyurethane film that provides a bacterial barrier and aesthetically pleasing outer surface to the dressing. The gel has a surface pH circa 4.2-4.6 arising from the presence of some carboxylic acid groups. These groups provide the acidity for the conversion of Sodium Nitrite to Nitric Oxide. As the carboxylic acid groups are covalently bound to the hydrogel network they are not released into the wound.

Description of Manufacturing Process

The hydrogel is manufactured from the list of ingredients set out below. The process of manufacture is as according to patents EP1100555B1 and EP110556B1, which are incorporated by reference in their entirety herein.

The ingredients are dispensed into a suitable mixing vessel (dispensing is controlled by weight) and stirred overnight. Once mixed, a portion of the liquid solution is dispensed onto a moving substrate (clear polyurethane film, Inspire 2304) at the required coat weight. Then a mesh made of polypropylene (RKW 20 g/m$^2$) is laid onto the top of the liquid formulation, which is then exposed to UV light and cured. A second layer is coated on top of the first at the required coat weight and exposed to UV light, thus making a "sandwich" with the mesh in the middle.

The hydrogel is cut to the required size and pouched, sealed and sterilised. The finished products are sterilised by gamma irradiation.

The components of the hydrogel component are:
Monomer, Sodium AMPS 2405A (58% solution in water) (Lubrizol)
Monomer, Acrylic Acid (BASF)
Glycerine BP, EP (H. Fosters)
Darocur 1173, 2-hydroxy-2-methylpropiophenone (BASF)
SR 344, poly (ethylene glycol) diacrylate (Sartomer)
Mesh, Carded non-woven 20 gsm (RKW-Group)
Inspire 2304, polyurethane film (Exopack)
70 micron, low density polyethylene, siliconised (Adcoat)
'NeoCarta,' peelable laminate (Safta)
The components of the nitrite layer are:
Mesh, Carded non-woven 20 gsm (RKW-Group)
'NeoCarta,' peelable laminate (Safta)
Sodium Nitrite, extra pure, Ph Eur, USP (Merck)
De-ionised water (First Water Ltd)

EXAMPLE 2

Treatment of Diabetic Foot Ulcer

A patient with diabetic foot ulceration was treated with a dressing according to the present invention. The patient was a 62 year old lady with long-standing diabetes and an ulcer on the dorsum of her left foot that had been present for a year. The ulcer had partially healed but was still present and the skin surrounding the ulcer was swollen and of poor quality.

The NOx dressing was applied for 1 hour and measurements of blood flow made at time 0, 20 mins and 60 mins. For comparison, blood flow was also measured in the contralateral foot, at the same time points.

Figure 2:
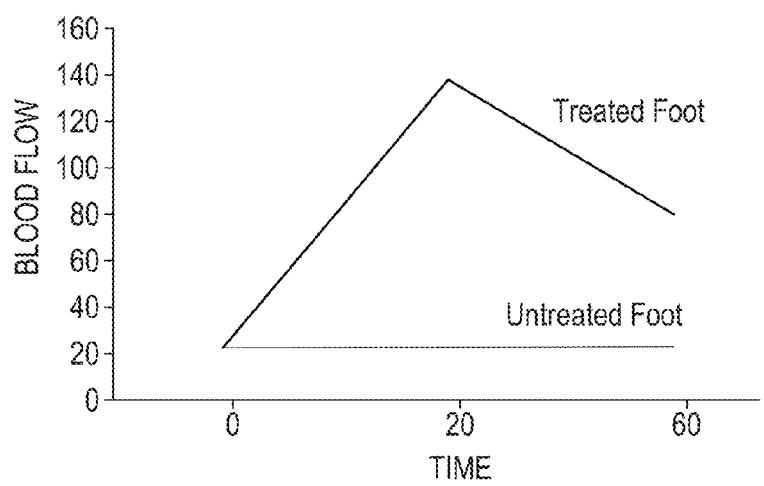
FIG. 2 shows changes in blood flow in treated and untreated feet in a patient with diabetes and a foot ulcer on one foot.

In the contralateral foot, the blood flow remained unchanged during the test period. By comparison, the blood flow in the treated foot increased by over 500% within 20 mins, and remained almost 300% above baseline at 1 hour (FIG. 2). In addition, there was a very noticeable effect at 1 hour. The blood flow in the contralateral foot remained low and sluggish. However, the blood flow in the treated foot not only increased in volume but also acquired a "pulsatile" form. This is vasomotion and is also perfectly normal in healthy skin. It is a combination of the heartbeat, which also was clearly seen in the traces after treatment with the NOx dressing, and the effect of respiration.

EXAMPLE 3

Acidifying Effect of Wound Dressing

Although normal skin is acidic, a wound is an alkaline environment. The chemical reaction occurring in the wound dressings of the invention depend on acid reacting with nitrite. Tests were therefore carried out to ensure that the dressing would be effective in a typical alkaline wound environment.

Firstly, studies were performed to test the dressing in a static skin wound model. In this experiment, the $NO_x$ dressing was applied to a cellulose pad soaked in Hanks solution (pH 7.1-7.5) that reflects changes in pH. Within five minutes the pH of the solution in the filter paper had dropped to 5.65 (3-sigma, 5.41-5.89). Within 15 minutes the pH of the filter pad had dropped to 5.08 (3-sigma, 4.62-5.54). The pH of the controls remained between 7-8 (7.27-7.85 from 7.04-7.62) during the time frame of the experiment. The Hanks solution contains phenol red, which at pH <6.8 is yellow, 6.8 to 8.2 is red and >8.2 is purple. Two samples with gel placed over them turned yellow within five minutes; the control was still red.

Figure 3:
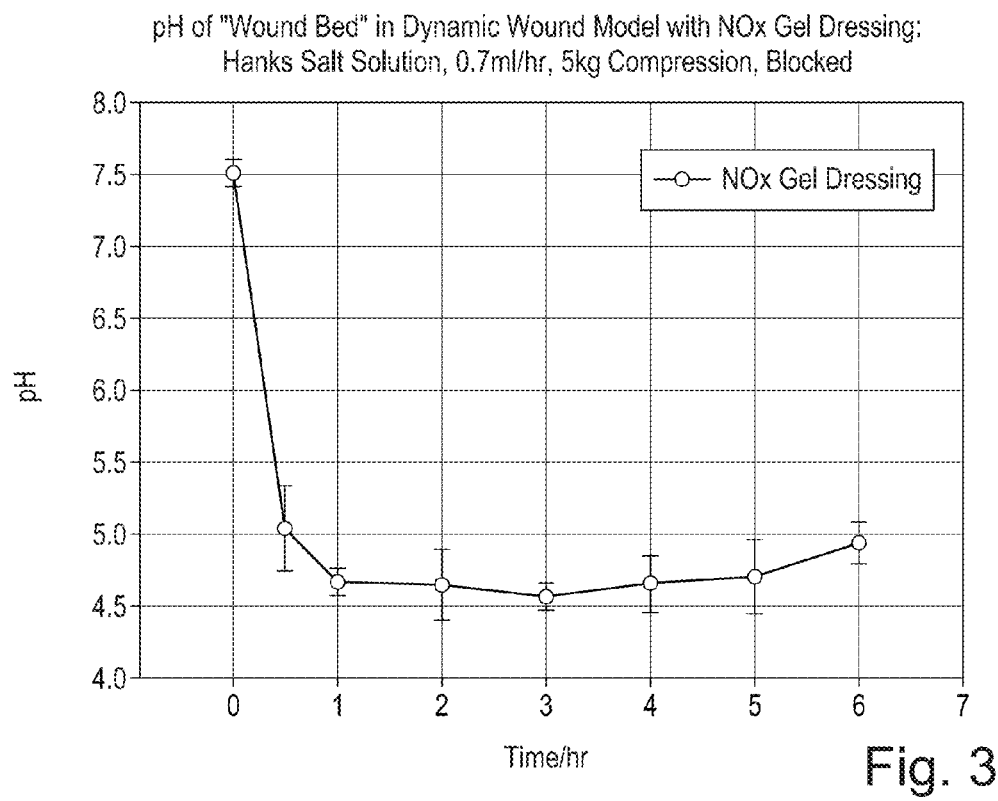
FIG. 3 shows short-term changes in pH after application of the NOx gel dressing.

The experiment with the cellulosic pads is a static experiment. In an in-vivo scenario the wound will constantly exude fluid of an alkaline pH. Therefore the dressing must be able to continually modify the environment when alkaline fluid is infused. To evaluate this the NOx Gel Dressing was placed on a Dynamic Wound Model ("DWM", WRAP model (Surgical Materials Testing Laboratory, UK)). The DWM simulates a wound by constantly infusing Hanks' Solution into a wound bed (two cellulosic filter papers) over an allotted period of time. The dressing has 5 kg of weight placed onto it to simulate compression bandaging. The pH was monitored over the first 6 hours (FIG. 3)

Figure 4:
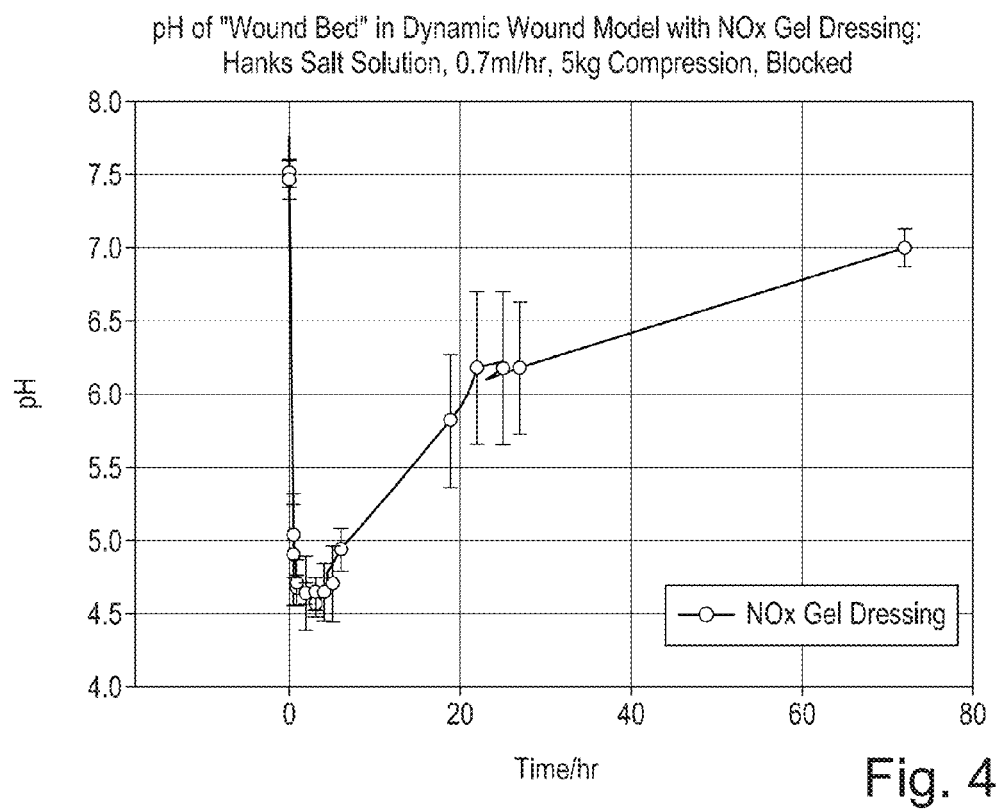
FIG. 4 shows changes in pH over 72 hrs after application of the NOx gel dressing.

The dressing was left on the wound model for 72 hours and the pH of the "wound bed" measured at various timepoints (FIG. 4). The rate of infusion was 0.7 ml/hr, meaning a total of 50 ml of alkaline solution was delivered to the dressing.

These findings were important because they show that dressing provides an acidifying effect, despite the alkaline environment of a wound.

EXAMPLE 4

Increase of Blood Flow within Diabetic Foot Ulcer Wound Bed

Blood flow within the diabetic foot ulcer wound bed, as measured using Laser Doppler Fluxmetry (LDF), increased significantly from baseline using a 2 part nitric oxide generating dressing in the absence of a reductant.

6 patients with diabetic foot ulcers, of at least 25 $mm^2$ that had been present for more than 6 weeks, were consented to join the clinical study. In a controlled environment perfusion units, the accepted measure of blood flow, were monitored using a Moor VMS LDF2 within the wound centre and around the wound bed. Measurements were taken at baseline on the affected foot and at an equivalent site on the contralateral foot. The primary layer and secondary hydrogel top layer, as described in Example 1, were applied to the wound. After 30 minutes the dressing was removed and the blood flow measured in and around the wound bed and at the contralateral foot site. The dressing was reapplied for a further 30 minutes before being removed and again blood flow measurements were taken in and around the wound site and the contralateral foot site.

Figure 5:
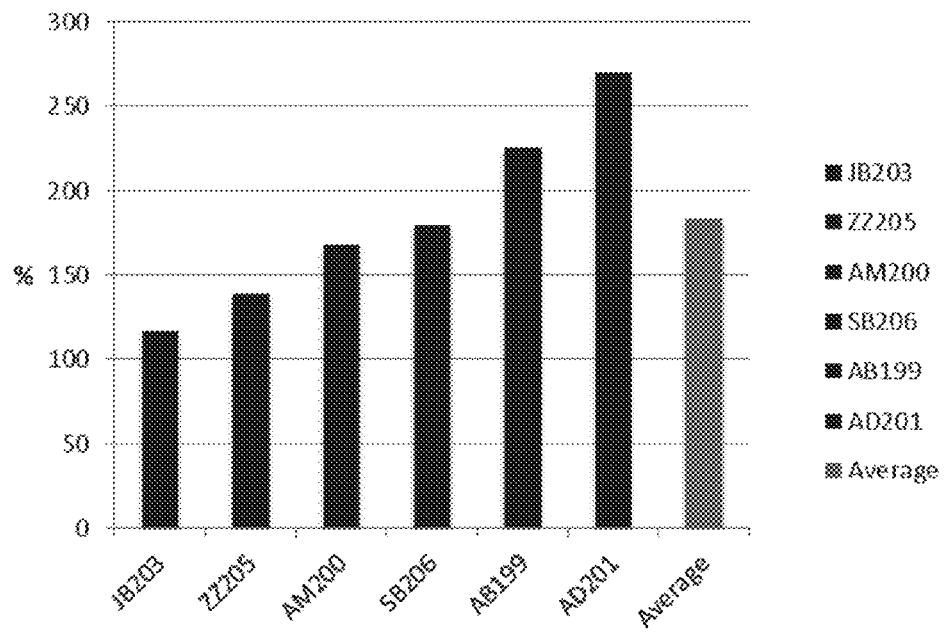
FIG. 5 shows peak blood flow in the wound bed of diabetic foot ulcers as % of baseline in patients treated with a dressing system of the invention.

The average increase in blood flow units was 74.8PU (p=0.012) however as the baseline blood flow in the study subjects ranged from 24.6 to 294.9 it is also pertinent to report that the average percentage increase in blood flow was 82.8% (p=0.016). The full range of increases can be seen in FIG. 5.

EXAMPLE 5

Stimulation of Healing in Diabetic Foot Ulcers

The 2 layer, reductant free, nitric oxide generating dressing stimulated healing in diabetic foot ulcers in a clinical study.

In an ongoing randomised, controlled clinical study examining healing in ulcers greater than 25 $mm^2$ in area with mild or moderate ischaemia, 4 patients early in the recruitment have already shown a significant response measured by reduction in area. The patients' ulcers were measured at baseline using a SilhouetteStar™ camera and software, which accurately measures perimeter and area of the ulcer. Patients are treated using a primary layer and a secondary hydrogel top layer, as described in Example 1. The dressing system was changed at least every 48 hours. Patients were re-examined weekly for the first month and every 2 weeks thereafter. Images and measurements were taken at each re-examination using the SilhouetteStar™ camera.

The initial results are:

Ulcer 1, on a 58 year old patient had been present for 6 weeks prior to treatment. At baseline the ulcer was 0.9 cm$^2$. The ulcer completely healed within 5 weeks of commencing treatment with the nitric oxide dressing.

Ulcer 2, on a 58 year old patient had been present for 22 weeks prior to treatment. At baseline the ulcer was 4.3 cm$^2$. The ulcer was still healing and measured 0.3 cm$^2$ (7% of the original area) after 12 weeks of application of nitric oxide dressing.

Ulcer 3, on a 45 year old patient had been present for 12 weeks prior to treatment. At baseline the ulcer was 0.3 cm$^2$. The ulcer completely healed within 4 weeks of commencing application of the nitric oxide dressing.

Ulcer 4, on a 75 year old patient had been present for over 12 months prior to treatment. At baseline the ulcer was 0.3 cm$^2$. The ulcer completely healed within 9 weeks of commencing application of the nitric oxide dressing.

Figure 6:
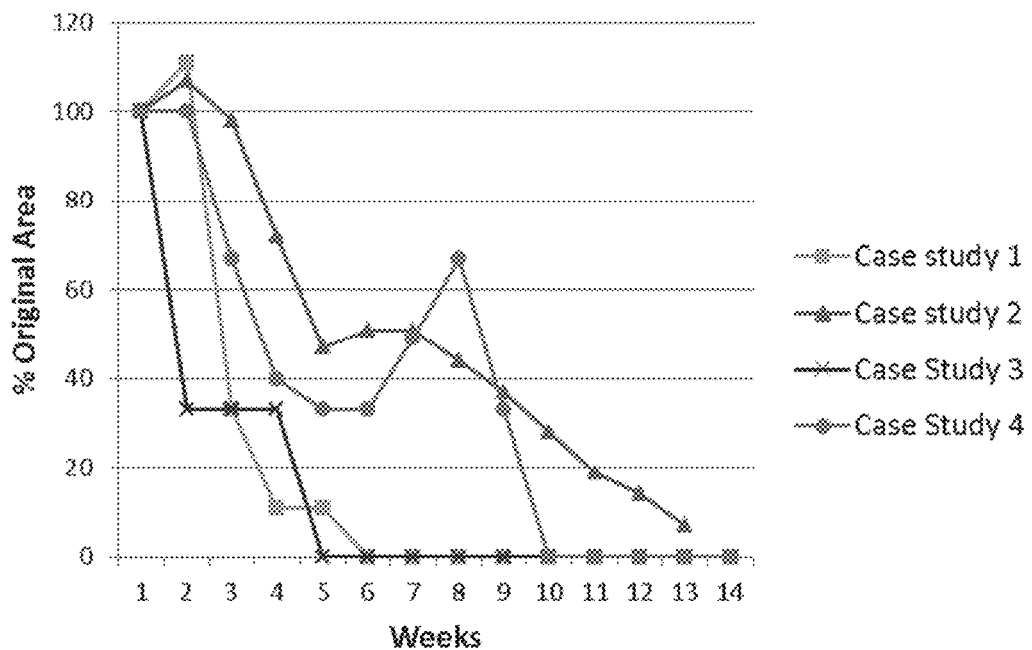
FIG. 6 shows the reduction in size of 4 diabetic ulcers over time as % of original wound area.

FIG. 6 shows the healing of the wounds over time.

EXAMPLE 6

Nitric Oxide Production from Dressing System of the Invention

The amount of Nitric Oxide produced by dressing systems of the invention was determined by detecting the gas evolved from the dressing system by the chemiluminescence of its reaction with ozone. The NO concentration was determined with a NOx analyser (Thermo Scientific, UK).

Primary Layer: Wound Contact Mesh (containing 0.1M Sodium Nitrite)

The Mesh is a polypropylene mesh (RKW-Group), imbibed with 0.1M Sodium Nitrite solution, from Sodium Nitrite Extra Pure ph Eur, USP Merck and deionised water.

Description of Manufacturing Process

Sodium nitrite is weighed into a suitably sized vessel and then transferred carefully into a known volume of deionised water, which is then stirred until dissolution is complete to make a solution of appropriate concentration (0.1M). In this embodiment the sodium nitrite solution is dispensed onto the mesh (25 cm$^2$) and then placed into each petri dish for a minimum time to imbibe the mesh with the sodium nitrite solution. The finished products are sterilised by irradiation. The weight of nitrite solution entrapped within each mesh was circa 0.4 g in this example.

Secondary Layer: Hydrogel Top Layer

Figure 7:
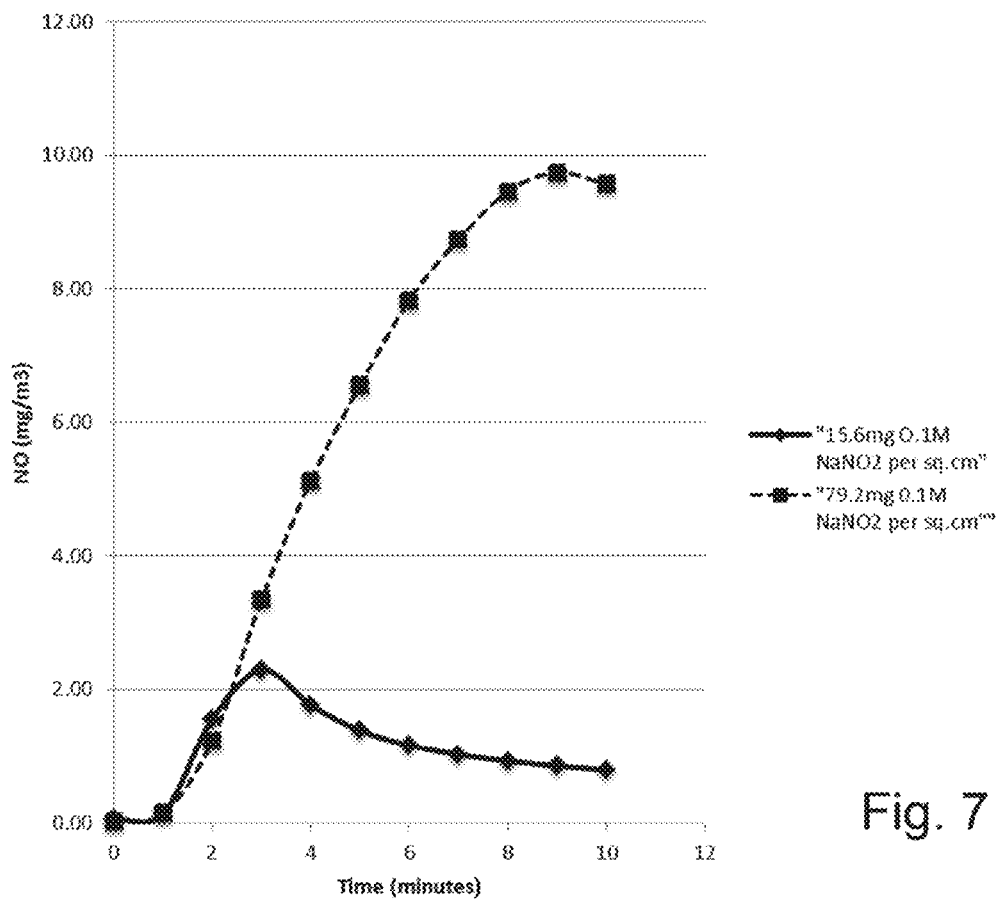
FIG. 7 shows the amount of nitric oxide released from 0.1M sodium nitrite solutions over time when the amount (by weight) of sodium nitrite solution in contact with the hydrogel is varied.

A sheet hydrogel from Example 1 (100 cm$^2$) was placed onto either one mesh (15.6 mg nitrite solution per cm$^2$ of mesh in contact with the hydrogel) or 5 meshes (79.2 mg nitrite solution per cm$^2$ of mesh in contact with the hydrogel) overlaying a glass sinter leading to the NOx analyser. The evolution of nitric oxide was monitored over a ten minute time period. The data obtained are shown in FIG. 7. As can be seen from FIG. 7, the amount of nitric oxide produced was much greater and the duration of release much longer in the experiment where the 5 meshes were used.

The data in FIG. 7 show that amount and duration of release is dependent on the amount (weight) of sodium nitrite solution constrained to the area of contact with the acidifying sheet hydrogel.

EXAMPLE 7

Nitric Oxide Production from Dressing System of the Invention

The amount of Nitric Oxide produced by dressing systems of the invention was determined by detecting the gas evolved from the dressing system by the chemiluminescence of its reaction with ozone. The NO concentration was determined with a NOx analyser (Thermo Scientific, UK).

Primary Layer: Wound Contact Mesh (containing 0.1M Sodium Nitrite)

The Mesh is a polypropylene mesh (RKW-Group), imbibed with 0.1M Sodium Nitrite solution, from Sodium Nitrite Extra Pure ph Eur, USP Merck and deionised water.

Description of Manufacturing Process

Sodium nitrite is weighed into a suitably sized vessel and then transferred carefully into a known volume of deionised water, which is then stirred until dissolution is complete to make a solution of appropriate concentration (0.1M or 1.02M). In this embodiment the sodium nitrite solution is dispensed onto the mesh (25 cm$^2$) and then placed into each petri dish for a minimum time to imbibe the mesh with the sodium nitrite solution. The finished products are sterilised by irradiation. The weight of nitrite solution entrapped within each mesh was circa 0.4 g in this example.

Secondary Layer: Hydrogel Top Layer

A sheet hydrogel from Example 1 (100 cm$^2$) was placed onto one mesh comprising 15.6 mg 0.1M nitrite solution per cm$^2$ of mesh in contact with the hydrogel and or 15.6 mg 1.02M nitrite solution per cm$^2$ of mesh in contact with the hydrogel overlaying a glass sinter leading to the NOx analyser. The evolution of nitric oxide was monitored over a ten minute time period. The data obtained are shown in FIG. 8.

Figure 8:
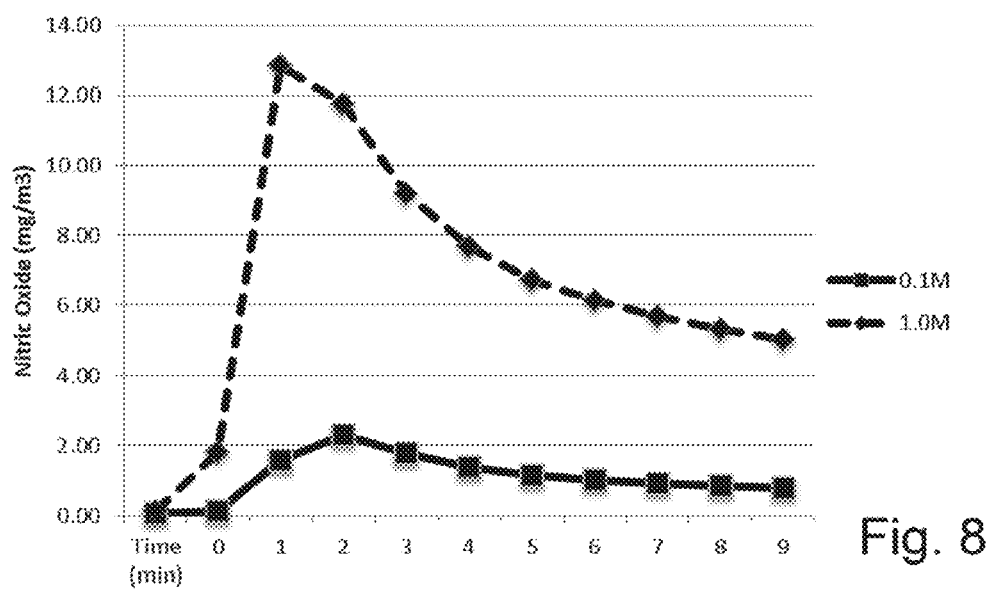
FIG. 8 shows the amount of nitric oxide released from 0.1M and 1.02M sodium nitrite solutions over time.

The data in FIG. 8 show that amount of release is dependent on the concentration of sodium nitrite solution constrained to the area of contact with the acidifying sheet hydrogel.

EXAMPLE 8

Use of Dressing System of the Invention as Pre-Treatment for Anaesthetic

Control

Firstly, as a control, 0.2 g of a 2% (w/v) lidocaine hydrochloride anaesthetic spray (Boots UK) was dispensed onto a circa 3 cm×6 cm area of the the skin on the underside of the left forearm of a healthy male volunteer and left 5 minutes. After 5 minutes the skin was pinched by another party using their thumb and forefinger. The healthy male volunteer was then asked to rate the level of pain experienced. The volunteer reported that the pain level was moderate to high, rated 5-6 on a visual analogue scale of 0-10 where 0 is no pain and 10 is worst possible pain.

Experiment

A 3 cm×6 cm mesh comprising 8 mg 1.0M NaNO$_2$ solution per cm$^2$ of mesh was placed on intact skin on the underside of the right forearm of the same healthy male volunteer as in the the previous example. A 6 cm×10 cm Sheet of hydrogel from Example 1 was placed over the nitrite solution containing mesh and left in place for 5 minutes. The sheet hydrogel and mesh were removed. The area of skin covered by the mesh had turned red due to vasodilation. 0.2 g of a 2% (w/v) lidocaine hydrochloride anaesthetic spray (Boots UK) was dispensed onto the vasodilated area of the the skin previously covered by the mesh and left 5 minutes. After 5 minutes the skin was pinched by another party using the thumb and forefinger. The male volunteer was then asked to rate the level of pain experienced. The experiment was then repeated on a different area of the forearm. In both cases the volunteer noted a significant reduction in pain, rated 2 on a visual analogue scale, when compared to the treatment of the left forearm using only the lidocaine hydrochloride anaesthetic spray as the treatment. The reduction in pain experienced by the volunteer indicates that the nitric oxide producing dressing used as a pre treatment increases the effectiveness of a topically applied anaesthetic.

The invention claimed is:

1. A system comprising:
   (i) a layer containing a nitrite; and
   (ii) a hydrogel that contains hydrogen ions,
   wherein the system does not contain a thiol or a reductant.

2. The system according to claim 1, wherein the layer is a mesh.

3. The system according to claim 2, wherein the mesh is formed of a polymer.

4. The system according to claim 3, wherein the polymer is polypropylene.

5. The system according to claim 1, wherein the nitrite is an alkaline metal nitrite or an alkaline earth metal nitrite.

6. The system according to any claim 5, wherein the nitrite is sodium nitrite.

7. The system according to claim 1, wherein the system comprises a plurality of layers containing a nitrite.

8. The system according to claim 1, wherein the nitrite is present as a nitrite solution.

9. The system according to claim 1, wherein the hydrogel is partially hydrated.

10. The system according to claim 1, wherein the hydrogel is cross-linked.

11. The system according to claim 1, wherein the hydrogel is a co-polymer.

12. The system according to claim 11, wherein the hydrogel is a co-polymer of polysulfonate and acrylic acid.

13. A method of treating a condition associated with tissue ischaemia or a wound in a subject comprising administering to the subject a hydrogel that contains hydrogen ions simultaneously, separately or sequentially with a layer containing a nitrite.

14. A method for the treatment of a condition associated with tissue ischaemia or a wound, comprising administering the system according to claim 1 to a subject in need thereof.

15. The method according to claim 14, wherein the layer containing the nitrite is administered simultaneously with the hydrogel that contains hydrogen ions or is administered prior to administration of the hydrogel that contains hydrogen ions.

16. A kit comprising a layer containing a nitrite and a hydrogel that contains hydrogen ions as a combined preparation.

17. The system according to claim 1 in combination with an aqueous-soluble drug.

18. A system comprising:
   (i) a layer containing a nitrite; and
   (ii) a hydrogel that contains hydrogen ions in combination with an anaesthetic.

19. The system according to claim 18, wherein the anaesthetic is selected from the group consisting of lignocaine (lidocaine), amethocaine (tetracaine), xylocaine, bupivacaine, prilocaine, ropivacaine, benzocaine, mepivocaine, cocaine or a mixture thereof.

20. A method of treatment or prevention of pain comprising administering a system comprising:
   (i) a layer containing a nitrite; and
   (ii) a hydrogel that contains hydrogen ions and an anaesthetic to a subject in need thereof.

21. The method according to claim 14, wherein the wound is an ulcer.

22. The method according to claim 21, wherein the ulcer is a leg ulcer, pressure ulcer or diabetic ulcer.

23. The method according to claim 14, wherein the wound is a skin donor site, a surgical wound, a burn, a laceration or an abrasion.

24. The method according to claim 14, wherein the condition associated with tissue ischaemia is Raynaud's syndrome or tissue ischaemia caused by septic shock.

* * * * *